/ United States Patent (12)
Grams et al.

(10) Patent No.: US 6,576,628 B1
(45) Date of Patent: Jun. 10, 2003

(54) 3-ARYL-SUCCINAMIDO-HYDROXAMIC ACIDS, METHODS FOR PRODUCING SAID ACIDS AND MEDICAMENTS CONTAINING THE SAME

(75) Inventors: Frank Grams, Mannheim (DE); Gerd Zimmermann, Mannheim (DE); Hans-Willi Krell, Penzberg (DE); Ernesto Menta, Cernusco sul Naviglio (IT); Herbert Leinert, Heppenheim (DE)

(73) Assignee: Roche Diagnostics GmbH, Mannhein (DE)

( * ) Notice: Subject to any disclaimer, the term of this patent is extended or adjusted under 35 U.S.C. 154(b) by 0 days.

(21) Appl. No.: 09/486,038

(22) PCT Filed: Aug. 18, 1998

(86) PCT No.: PCT/EP98/05243

§ 371 (c)(1),
(2), (4) Date: Jul. 6, 2000

(87) PCT Pub. No.: WO99/09003

PCT Pub. Date: Feb. 25, 1999

(30) Foreign Application Priority Data

Aug. 19, 1997 (DE) ............................................ 97114255

(51) Int. Cl.[7] ................... C07C 259/06; C07D 213/95; C07D 295/185; A61K 31/16; A61P 9/10
(52) U.S. Cl. ................................ 514/228.2; 514/228.2; 514/237; 514/252; 514/374; 514/378; 514/616; 544/88; 544/98; 544/168; 546/309; 548/237; 548/215; 548/240; 562/623

(58) Field of Search .............................. 514/228.2, 237, 514/252, 374, 378, 616; 544/88, 98, 168; 546/309; 548/237, 215, 240; 564/616; 562/623

(56) References Cited

FOREIGN PATENT DOCUMENTS

| GB | 2 268 933 | 1/1994 |
|----|-----------|--------|
| WO | 95 19956 | 7/1995 |
| WO | 95 19957 | 7/1995 |

*Primary Examiner*—Mukund J. Shah
*Assistant Examiner*—Thomas McKenzie
(74) *Attorney, Agent, or Firm*—Arent Fox Kintner Plotkin & Kahn, PLLC

(57) ABSTRACT

The invention relates to inhibitors of matrix metalloproteases, more specifically a 3-aryl-succinamido-hydroxamic acid of formula (I)

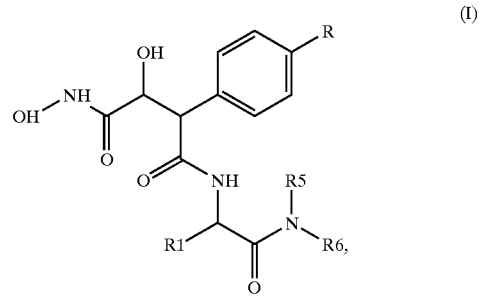

and its salt, ester and derivative thereof, along with methods of producing a compound of formula (I) and pharmaceutical compositions thereof.

18 Claims, No Drawings

3-ARYL-SUCCINAMIDO-HYDROXAMIC ACIDS, METHODS FOR PRODUCING SAID ACIDS AND MEDICAMENTS CONTAINING THE SAME

The present application concerns inhibitors of matrix metalloproteases. In particular it concerns 3-aryl-succinamido-hydroxamic acids.

In healthy tissue there is an equilibrium between synthesis and degradation of the extracellular matrix. The extracellular matrix is mainly degraded by proteases of the matrix metalloprotease (MMP) family. Examples of members of this family are collagenases, stromelysins and gelatinases. In healthy tissue this degradation is regulated by inhibition with TIMPs (tissue inhibitor of metalloproteases). This equilibrium between matrix metalloproteases and TIMPs is disturbed in various diseases such as rheumatoid and osteoarthritis, multiple sclerosis, metastasis and invasion of tumours, cornea ulcer, meningitis, cardiovascular diseases such as restenosis and arteriosclerosis as well as diseases of bones and gums. Many examples show that an inhibition of these enzymes can have a positive influence on the clinical picture of these diseases (Beckett et al., 1996).

The two gelatinases A (MMP-2) and B (MMP-9) appear to be the most important MMPs for metastasis and invasion. A selective inhibition of these two enzymes would be desirable. The furthest developed substance at present in this area, Marimastat, which is in clinical phase III is active but exhibits major side-effects such as muscle pain. In its present form Marimastat is a broad-range MMP inhibitor and consequently MMPs like MMP1 which are absolutely essential for tissue metabolism are also inhibited. It is generally assumed that the side-effects are due to the non-specificity.

It has now surprisingly been found that the new 3-aryl-succinamido-propionohydroxamic acids have a more favourable pharmacological profile than Marimastat. These substances differ inter alia from Marimastat by an aryl substitution at position 3 of the succinyl residue. The specificity with respect to gelatinases is considerably improved in the new compounds or rather is now present for the first time. I.e. it is possible to avoid inhibition of MMP1 and other important enzymes.

The present application concerns substances of the general formula I

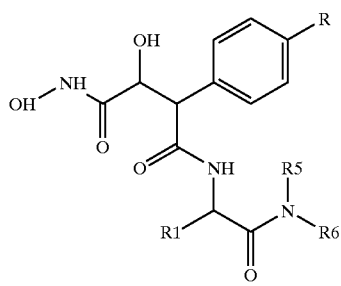
(I)

In order to achieve an optimal inhibition of the gelatinases, the residues R and R1 of the compounds of the general formula I should have certain hydrophobicities. A suitable parameter for this is clogP which can be determined with the aid of "PCModels clogp3" from Daylight Chemical Information Systems Inc. (1993). The coefficients are based on Hansch, C. & Leo, A.: Substituent Constants for Correlation Analysis in Chemistry and Biology. Wiley Interscience New York (1979), whereas the algorithm is based on the following citation: Chou, J. & Jurs, P., J. Chem. Inf. Comput. Sci. 19, 172 (1979). The fragments are entered as complete molecules for the calculation i.e. not as a radical or ion. In order to get informative values the clogP values for R are determined together with the neighbouring phenyl ring (Ph-R fragments). The clogP values for the residue R1 are determined together with the neighbouring carbonyl and amino group as (CHO)(NH$_2$)CHR1 (aminocarbonyl-R1 fragments).

Examples for Ph-R

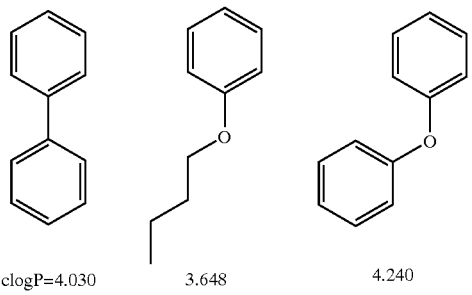

clogP=4.030    3.648    4.240

Examples for aminocarbonyl-R1:

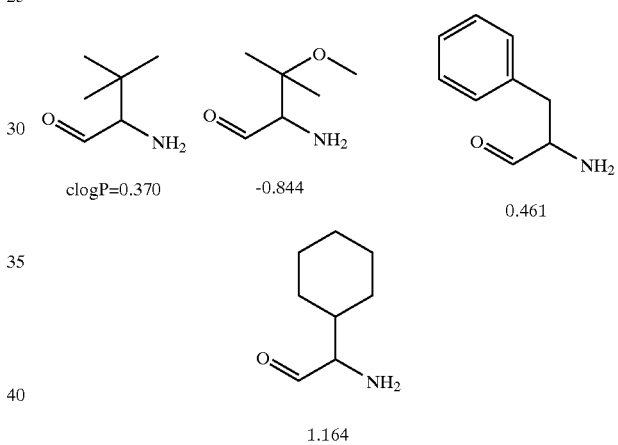

clogP=0.370    −0.844    0.461

1.164

The clogP values for R in the form of Ph-R fragments in the compounds of the present invention are 2.0 to 6.0, preferably 2.5 to 5.0, particularly preferably 3.0 to 4.5.

The clogP values for R1 in the form of aminocarbonyl-R1 fragments in the compounds of the present invention are between −1.5 and 2.0, preferably between −1.2 and 1.5, particularly preferably between −1.0 and 1.2.

The present application therefore concerns substances of the general formula I

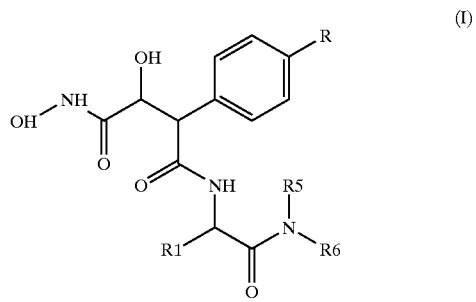
(I)

in which
- R as a Ph-R fragment has a clogP value between 2.0 and 6.0, preferably between 2.5 and 5.0 and particularly preferably between 3.0 and 4.5,
- R1 as an aminocarbonyl-R1 fragment has a clogP value between −1.5 and 2.0, preferably between −1.2 and 1.5 and particularly preferably between −1.0 and 1.2 and
- R5 denotes hydrogen or a $C_1$–$C_8$ alkyl residue
- R6 denotes hydrogen, an optionally substituted $C_1$–$C_8$ alkyl or an optionally substituted monocyclic or bicyclic cycloalkyl, aryl, heteroaryl, aralkyl or alkylheteroaryl residue, or
- R5 and R6 together with the N atom denote a saturated or unsaturated 5-membered or 6-membered ring which contains at most one additional heteroatom, pharmacologically compatible salts, esters and derivatives thereof which are metabolized in vivo into compounds of the general formula I as well as the use of these compounds for the production of pharmaceutical preparations.

Alternatively the subject matter of the present application can be represented as compounds of the general formula I:

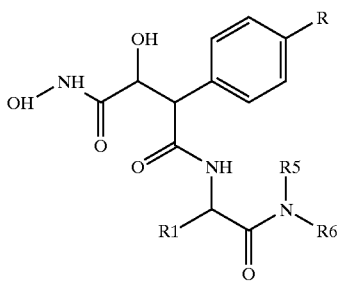

(I)

in which
- R denotes an optionally substituted $C_1$–$C_8$ alkyl, or an optionally substituted monocyclic or bicyclic cycloalkyl, aryl, heteroaryl, aryloxy, heteroaryloxy, or aralkyl residue,
- R1 denotes an optionally substituted $C_1$–$C_8$ alkyl or an optionally substituted monocyclic or bicyclic cycloalkyl, aryl, heteroaryl, aralkyl or alkylheteroaryl residue,
- R5 denotes hydrogen or a $C_1$–$C_8$ alkyl residue
- R6 denotes hydrogen, an optionally substituted $C_1$–$C_8$ alkyl or an optionally substituted monocyclic or bicyclic cycloalkyl, aryl, heteroaryl, aralkyl or alkylheteroaryl residue, or
- R5 and R6 together with the N atom denote a saturated or unsaturated 5-membered or 6-membered ring which contains at most one additional heteroatom, pharmacologically compatible salts, esters and derivatives thereof which are metabolized in vivo into compounds of the general formula I as well as the use of these compounds for the production of pharmaceutical preparations.

The residues listed under R, R1 and R6 can, independently of one another, be optionally substituted once, twice or three times by halogen, hydroxy, thio, alkyl, $C_3$–$C_8$ cycloalkyl, $C_4$–$C_8$ cycloalkenyl, hydroxyalkyl, alkoxy, hydroxyalkoxy, chloroalkoxy, alkylthio, alkylsulfinyl, alkylsulfonyl, amino, alkylamino, dialkylamino, nitro, carboxyl, carboxamido, alkoxycarbonyl, alkoxycarbonylalkyl, perfluoroalkyl or amino or aminocarbonyl optionally substituted once or twice by lower alkyl, nitrile, oxo or acyl.

In this connection a halogen, hydroxy, oxo, thio, alkoxy, ω-hydroxyalkoxy, ω-chloroalkoxy, alkylthio, amino, aminocarbonyl, carboxyl and acyl group are preferred. Methyl, halogen and hydroxyl are particularly preferred.

If they are substituted a single substitution is preferred.

If not stated otherwise cycloalkyl denotes a saturated mono or polyunsaturated carbocycle or heterocycle containing 3 to 8 structural atoms, preferably 5–7 structural atoms which can optionally be interrupted once or several times by heteroatoms such as nitrogen, oxygen or sulphur and in particular denotes a cyclopentyl, cyclohexyl, cycloheptyl, morpholinyl, thiamorpholinyl, piperidinyl, piperazinyl, tetrahydrofuryl or tetrahydropyranyl residue.

The alkyl residue in aralkyl and heteroalkyl in R, R1 and R6 denotes independently of one another $C_1$ or $C_2$ alkyl.

Acyl in the residues R, R1 and R6 denotes above all the acetyl group.

If not stated otherwise in the residues R, R1 and R6 alkyl alone or in combination e.g. with alkoxy, alkylthio, arylsulfonyl, alkylsulfonyl, alkylamino-carbonyl, arylaminocarbonyl, alkylamino, alkoxycarbonyl, aryloxycarbonyl, alkylaminothiocarbonyl, arylaminothiocarbonyl, denotes a straight-chained or branched, saturated or unsaturated residue with 1–3 carbon atoms such as methyl, ethyl, propyl, isopropyl, allyl or propinyl.

$C_1$–$C_8$ alkyl in the residues R, R1, R5 and R6 denotes independently of one another a straight-chained, branched, saturated or unsaturated residue containing 1 to 8 carbon atoms which can be interrupted by 1 or 2 heteroatoms such as O, N or S, where no interruption or an interruption by oxygen is preferred and in the case of an interruption by oxygen $C_1$–$C_7$ alkoxy is particularly preferred. Examples of $C_1$–$C_8$ alkyl residues are methyl, ethyl, propyl, pentyl, octyl, allyl, propargyl, 2,4-pentadienyl, isopropyl, sec.butyl, tert.butyl, 3-methyl-butyl, 2-hydroxy-hexyl, n-butoxy, hexyloxy, $C(CH_3)_2$OMe in particular tert. butyl, n-butoxy, hexyloxy, $C(CM_3)_2$oMe.

Aryl is understood as a phenyl or naphthyl residue which can be optionally substituted especially by halogen, alkyl or alkoxy. A phenyl residue is preferred.

Halogen is understood as chlorine, bromine or iodine, preferably chlorine.

Structural atoms are understood as C, N, O and S and heteroatoms are understood as N, O and S.

The heteroaryl residues listed for R, R1 and R6 denote independently of one another a pyridine, pyrimidine, pyridazine, pyrazine, piperazine, imidazole, furan, oxazole, isothiazole, isooxazole, 1,2,3-triazole or 1,2,4-triazole, thiazole, thiophene or indole ring, preferably a pyridine, imidazole or thiophene ring.

The bicycles listed under R, R1 and R6 are preferably residues such as naphthyl, tetrahydronaphthyl, dekalinyl, quinolyl, isoquinolyl, tetrahydroquinolyl, tetrahydroisoquinolyl, indolyl, benzimidazolyl, indazolyl, oxindolyl, benzofuranyl, benzothienyl, benzthiazolyl, benzoxazolyl or a purinyl residue, in particular a naphthyl, quinolyl, isoquinolyl, tetrahydroquinolyl, indolyl or benzimidazolyl residue.

Preferred residues for R are 4 to 7 structural atoms for alkyl and cycloalkyl, and 5 to 10 and particularly preferably 6 to 8 structural atoms are preferred for aryl, bicyclic and heteroaryl residues.

Preferred residues for R1 are 1 to 12 structural atoms particularly preferably 3 to 10 structural atoms.

Especially preferred residues for R are: —O-phenyl(p-R2), phenyl(p-R2), n-butoxy, hexyloxy in which R2 represents a small substituent such as hydrogen, halogen, methyl or hydroxyl; especially preferred residues for R are —O-phenyl, phenyl and n-butoxy.

Especially preferred residues for R1 are the residues benzyl, phenyl, tert.butyl or C(CH$_3$)$_2$OMe and in particular tert.butyl.

Preferred residues for R5 are hydrogen, methyl and ethyl; hydrogen is particularly preferred.

Preferred residue for R6 are methyl and ethyl, phenyl and pyridyl; methyl is particularly preferred.

If R5 and R6 form a ring this preferably contains oxygen and is particularly preferably morpholino.

The invention in addition concerns all optical isomers and racemates. The following optical isomers are preferred: C2 of the succinylhydroxamic acid and Cα of the amino-acid amide in the S configuration and C3 of the succinic acid parent substance in the R configuration.

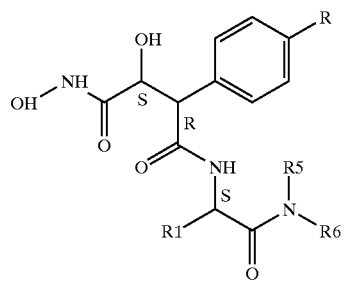

The compounds of the invention of the general formula I can be synthesized by known processes. The optical isomers can be separated by known methods. Whenever appropriate the described processes relate to the separation of final products and/or precursors. The diasteromeric salts are either formed from the racemic mixtures by reaction with an optically active acid such as D- or L-tartaric acid, mandelic acid, malic acid, lactic acid or camphorsulfonic acid or with an optically active amine such as D- or L-α-phenylethyl-amine, ephedrine, quinidine or cinquonidine which can be separated by crystallization, or the optical isomers are separated by HPLC. Another method of separating optical isomers is an enzymatic separation during synthesis and/or synthesis of intermediate products.

The compounds of the general formula I are obtainable by (a) Reacting a carboxylic acid of the general formula II in which R, R1, R5 and R6 have the above-mentioned meanings and in which the alcoholic hydroxy group can be present free or protected for example by ester formation with acetic acid,

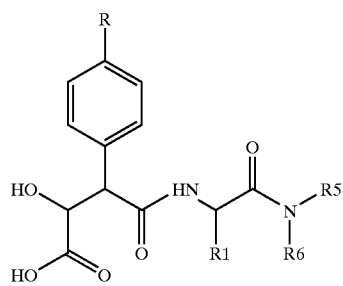

with hydroxylamine or with an O-protected or N,O-protected hydroxylamine and subsequently cleaving the protecting group.

For these reactions carboxylic acids can be activated by methods known from peptide chemistry. For example carboxylic acids can be activated directly by reaction with chloroformic esters, carbodiimides, N,N'-carbonyl-diimidazole, 2-chloro-N-methylpyridinium iodide or an intermediate reaction can be carried out to form active esters such as pentafluorophenyl, N-hydroxysuccinimide, N-hydroxybenzotriazole esters which can then be reacted with hydroxylamine or a protected hydroxylamine. After completion of the reaction of a protected hydroxylamine derivative, the protecting groups are cleaved off by known methods. Examples of protected hydroxylamines are O-benzylhydroxylamine, O-p-methoxybenzylhydroxylamine, O-trimethylsilylhydroxylamine, and O-tert-butyl-hydroxylamine, N,O-dibenzylhydroxylamine and N,O-bis-p-methoxybenzyl-hydroxylamine. The protecting groups can be cleaved in the case of benzyl or p-methoxybenzyl groups by hydrogenolysis or in the latter case or in the case of the O-tert-butyl group also by acid hydrolysis. A trimethylsilyl protecting group can be hydrolysed by water.

(b) As an alternative to (a), the compounds of formula I can be prepared by reacting a 1,3-dioxolan-4-one of the general formula III in which R3 and R4 represent hydrogen, lower alkyl or phenyl and preferably methyl with hydroxylamine.

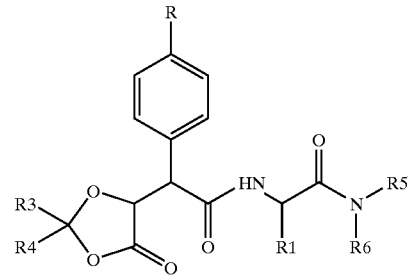

The compounds of the general structure II can be prepared by alkaline hydrolysis from compounds of the structure III.

Compounds of the general structure III are obtainable by coupling a 2-aryl-3-hydroxy-succinic acid of the general structure IVa in which R, R3 and R4 have the aforementioned meaning and whose hydroxy group and the neighbouring COOH group are protected with formation of a 1,3-dioxolan-4-one structure,

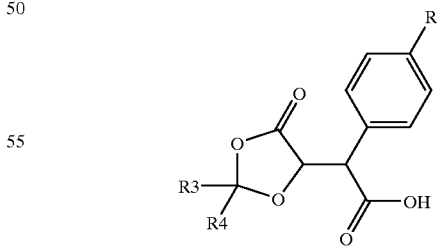

with racemic or optically homogeneous α amino acids e.g. (R) or (S)-tert-butyl-glycine-N-methylamide by methods which are known from peptide chemistry. For example active esters such as N-hydroxysuccinimide, 1-hydroxybenzotriazole or pentafluorophenyl esters can be prepared by activating the COOH group in IVa by carbodiimides such as di-cyclohexylcarbodiimide or di-isopropylcarbodiimide which can then react with the free amino group of an α-amino-acid amide substituted on the amide group. These esters can also be prepared without isolation and reacted further. Other methods of activation include the preparation of mixed anhydrides by reacting the carboxylic acids with chloroformic acid esters or condensation reagents such as uronium salts e.g. 2H-(1H-benzotriazol-1-yl)-1,1,3,3-tetramethyl-uronium-tetrafluoroborate.

The carboxylic acids of formula IVa can be prepared by reacting α-formylarylacetic acids of the general formula V

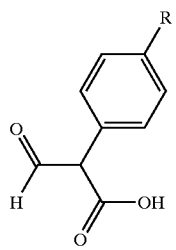

(V)

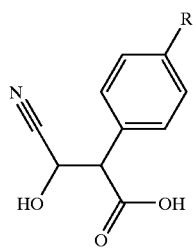

(VI)

in which R has the above-mentioned meaning with alkali cyanides or trimethylsilyl cyanide/zinc iodide, acid saponification of the cyanohydrins of the general structure VI which are obtained as intermediate products and subsequently protecting the hydroxy and the COOH group by an acid catalysed reaction with acetals or ketals e.g. 2,2-dimethoxypropane. The cyanohydrins can also be prepared as optically active molecules by enzymatic reaction of the compound of the general structure V catalysed by (R)- or (S)-oxynitrilases which yield stereospecifically the R or S compound respectively.

Alternatively compounds of formula IVa can be prepared by reducing oxalo-arylacetic esters e.g. with sodium borohydride, acid saponification of the esters and subsequent protection of the hydroxy group and the neighbouring COOH group by an acid catalysed reaction with acetals or ketals e.g. 2,2-dimethoxypropane.

Alkali salts, ammonium salts, acetates or hydrochloride are primarily used as pharmacologically compatible salts which are prepared in the usual manner e.g. by titrating the compounds with inorganic or organic bases or inorganic acids such as e.g. sodium hydroxide, potassium hydroxide, aqueous ammonia, amines such as triethylamine or hydrochloric acid. The salts are usually purified by reprecipitation from water/acetone.

The new substances according to the invention of formula I and salts thereof can be administered enterally or parenterally in a liquid or solid form. All the usual forms of administration come into consideration such as tablets, capsules, dragées, syrups, solutions, suspensions etc. Water is preferably used as an injection medium which contains the usual additives in injection solutions such as stabilizers, solubilizers and buffers.

Such additives are for example tartrate and citrate buffer, ethanol, complexing agents (such as ethylene diamine-tetraacetic acid and non-toxic salts thereof), high molecular polymers (such as liquid polyethylene oxide) to regulate viscosity. Liquid carriers for injection solutions must be sterile and are preferably filled into ampoules. Solid carriers are for example starch, lactose, mannitol, methylcellulose, talcum, highly dispersed silicic acids, higher molecular fatty acids (such as steric acid), gelatine, agar-agar, calcium phosphate, magnesium stearate, animal and vegetable fats, solid high molecular polymers (such as polyethylene glycols); suitable formulations for oral administration can if desired contain flavouring agents and sweeteners.

The dose can depend on various factors such as manner of administration, species, age and/or individual state. The daily doses to be administered are about 10–1000 mg/person, preferably 100–500 mg/person and can be taken once or divided over several applications.

Apart from the compounds stated in the examples and compounds that can be derived by combining all meanings of the substituents mentioned in the examples, the following 3-aryl-succinamido-hydroxamic acid derivatives are preferred in the sense of the present invention:

1. 2-(biphenyl-4-ylamino)-N1-(2,2-dimethyl-1-methyl-carbamoyl-propyl)-3,N4-dihydroxy-succinamide
2. 2-(biphenyl-4-ylamino)-N1-[2,2-dimethyl-1-(morpholin-4-ylcarbonyl)-propyl]-3,N4-dihydroxy-succinamide
3. 2-(biphenyl-4-ylamino)-N1-[2,2-dimethyl-1-(pyridin-2-ylcarbomoyl)-propyl]-3,N4-dihydroxy-succinamide
4. 2-(biphenyl-4-ylamino)-3,N4-dihydroxy-N1-(1-methyl-carbamoyl-2-phenyl-ethyl)-succinamide
5. N1-(1-benzyl-2-morpholin-4-yl-2-oxo-ethyl)-2-(bipheny-4-ylamino)-3,N4-dihydroxy-succinamide
6. 2-(biphenyl-4-ylamino)-3,N4-dihydroxy-N1-[2-phenyl-1-(pyridin-2-ylcarbamoyl)-ethyl]-succinamide
7. 2-(biphenyl-4-ylamino)-3,N4-dihydroxy-N1-[2-methoxy-2-methyl-1-methylcarbamoyl-propyl]-succinamide
8. 2-(biphenyl-4-ylamino)-3,N4-dihydroxy-N1-[2-methoxy-2-methyl-1-(morpholin-4-carbonyl)-propyl]-succinamide
9. 2-(biphenyl-4-ylamino)-3,N4-dihydroxy-N1-[2-methoxy-2-methyl-1-(pyridin-2-ylcarbamoyl)-propyl]-succinamide
10. N4-(2,2-dimethyl-1-methylcarbamoyl-propyl)-2N1-dihydroxy-3-(4-phenoxy-phenylamino)-succinamide
11. N-4-[2,2-dimethyl-1-(morpholin-4-carbonyl)-propyl]-2,N1-dihydroxy-3-(4-phenoxy-phenylamino)-succinamide
12. N4-[2,2-dimethyl-1-(pyridin-2-ylcarbamoyl)-propyl]-2,N1-dihydroxy-3-(4-phenoxy-phenylamino)-succinamide
13. 2,N1-dihydroxy-N4-(1-methylcarbamoyl-2-phenyl-ethyl)-3-(4-phenoxy-phenylamino)-succinamide
14. N4-(1-benzyl-2-morpholin-4-yl-2-oxo-ethyl)-2,N1-dihydroxy-3-(4-phenoxy-phenylamino)-succinamide
15. 2,N1-dihydroxy-3-(4-phenoxy-phenylamino)-N4-[2-phenyl-1-(pyridin-2-ylcarbamoyl)-ethyl]-succinamide
16. 2,N1-dihydroxy-N4-(2-methoxy-2-methyl-1-methyl-carbamoyl-propyl)-3-(4-phenoxy-phenylamino)-succinamide
17. 2,N1-dihydroxy-N4-[2-methoxy-2-methyl-1-(morpholin-4-carbonyl)-propyl]-3-(4-phenoxy-phenylamino)-succinamide
18. 2,N1-dihydroxy-N4-[2-methoxy-2-methyl-1-(pyridin-2-ylcarbamoyl)-propyl]-3-(4-phenoxy-phenylamino)-succinamide
19. 2-(4-butoxy-phenylamino)-N1-(2,2-dimethyl-1-methyl-carbamoyl-propyl)-3,N4-dihydroxy-succinamide
20. 2-(4-butoxy-phenylamino)-N1-[2,2-dimethyl-1-(morpholin-4-carbonyl)-propyl]-3,N4-dihydroxy-succinamide 21. 2-(4-butoxy-phenylamino)-N1-[2,2-dimethyl-1-(pyridin-2-ylcarbamoyl)-propyl]-3,N4-dihydroxy-succinamide
22. 2-(4-butoxy-phenylamino)-3,N4-dihydroxy-N1-(1-methylcarbamoyl-2-phenyl-ethyl)-succinamide
23. N1-(1-benzyl-2-morpholino-4-yl-2-oxo-ethyl)-2-(4-butoxy-phenylamino)-3,N4-dihydroxy-succinamide
24. 2-(4-butoxy-phenylamino)-3,N4-dihydroxy-N1-[2-phenyl-1-(pyridin-2-ylcarbamoyl)ethyl]-succinamide
25. 2-(4-butoxy-phenylamino)-3,N4-dihydroxy-N1-(2-methoxy-2-methyl-1-methylcarbamoyl-propyl)-succinamide
26. 2-(4-butoxy-phenylamino)-3,N4-dihydroxy-N1-[2-methoxy-2-methyl-1-(morpholin-4-carbonyl)-propyl]-succinamide
27. 2-(4-butoxy-phenylamino)-3,N4-dihydroxy-N1-[2-methoxy-2-methyl-1-(pyridin-2-ylcarbamoyl)-propyl]-succinamide
28. N1-(2,2-dimethyl-1-methylcarbamoyl-propyl)-2-(4-hexyloxy-phenylamino)-3,N4-dihydroxy-succinamide
29. N1-[2,2-dimethyl-1-(morpholin-4-carbonyl)-propyl]-2-(4-hexyloxy-phenylamino)-3N4-dihydroxy-succinamide
30. N1-[2,2-dimethyl-1-(pyridin-2-ylcarbamoyl)-propyl]-2-(4-hexyloxy-phenylamino)-3,N4-dihydroxy-succinamide
31. 2-(4-hexyloxy-phenylamino)-3,N4-dihydroxy-N1-(1-methylcarbamoyl-2-phenyl-ethyl)-succinamide
32. N1-(1-benzyl-2-morpholin-4-yl-2-oxo-ethyl)-2-(4-hexyloxy-phenylamino)-3,N4-dihydroxy-succinamide
33. 2-(4-hexyloxy-phenylamino)-3,N4-dihydroxy-N1-[2-phenyl-1-(pyridin-2-ylcarbamoyl)-ethyl]-succinamide
34. 2-(4-hexyloxy-phenylamino)-3,N4-dihydroxy-N1-(2-methoxy-2-methyl-1-methylcarbamoyl-propyl)-succinamide
35. 2-(4-hexyloxy-phenylamino)-3,N4-dihydroxy-N1-[2-methoxy-2-methyl-1-(morpholin-4-carbonyl)-propyl]-succinamide
36. 2-(4-hexyloxy-phenylamino)-3,N4-dihydroxy-N1-[2-methoxy-2-methyl-1-(pyridin-2-ylcarbamoyl)-propyl]-succinamide

EXAMPLE 1

2-Biphenyl-4-yl-N1-((1S)-2,2-dimethyl-1-methylcarbamoyl-propyl)-3,N4-dihydroxy-succinamide 1.1 α-Formyl-biphenylacetic acid ethyl ester A mixture of 24 g biphenylacetic acid ethyl ester and 8.2 g ethyl formate is added dropwise while stirring to a suspension of 2.4 g sodium hydride in 250 ml ether. The reaction mixture is stirred for 2 hours at room temperature and cold water is carefully added. The aqueous phase is acidified to pH 2 and the product is extracted with ether. The extract is dried and concentrated by evaporation.

1.2. 2-Biphenyl-3-hydroxy-succinic acid 2 g trimethylsilyl cyanide and a catalytic amount of zinc iodide are added to a solution of 5.7 g α-formyl-biphenylacetic acid ethyl ester in 70 ml dichloro-methane. The mixture is stirred overnight at room temperature and concentrated by evaporation. 6 N HCl is added to the residue and boiled under reflux to saponify the nitrile, trimethylsilyl and ester group. The product is isolated by extraction with ether.

1.3 α-2,2-Dimethyl-1,3-dioxolan-4-one-5-yl-biphenyl-acetic acid 3.14 g 2-biphenyl-3-hydroxy-succinic acid is dissolved in 100 ml 2,2-dimethoxy propane and 30 ml DMF, a catalytic amount of p-toluenesulfonic acid is added and it is stirred overnight at 30–40° C. The solvent is removed by evaporation and the crude product is used in the next step.

1.4 α-2,2-Dimethyl-1,3-dioxolan-4-one-5-yl-biphenyl-acetyl-(S)-tert.butyl-glycine-N'-methylamide 0.6 g α-2,2-dimethyl-1,3-dioxolan-4-one-5-yl-biphenyl acetic acid and 0.3 g (S)-tert.-butyl-glycine-N'-methylamide are dissolved in 30 ml methylene chloride and 0.2 g diisopropyl-ethylamine is added. 0.5 g 2H-(1H-benzotriazol-1-yl)-1,1,3,3-tetramethyluronium tetra-fluoroborate is added and the mixture is stirred overnight. Approximately 200 ml acetic ester is added and the organic phase is washed successively with sodium bicarbonate solution, 0.5 N hydrochloric acid and again with sodium bicarbonate solution. The organic phase is dried and concentrated by evaporation and the residue is triturated with ether.

1.5 2-Biphenyl-4-yl-N1-((1S)-2,2-dimethyl-1-methyl-carbamoyl-propyl)-3,N4-dihydroxy-succinamide 0.14 g sodium methylate is added to a solution of 0.14 g hydroxylamine hydrochloride in methanol and the mixture is stirred for two hours at room temperature. The precipitate is removed by filtration and the filtrate is cooled in an ice bath. 0.9 g of the R,S-α-2,2-dimethyl-1,3-dioxolan-4-one-5-yl-biphenylacetyl-tert-glycine-N'-methylamide obtained above is added in portions. The mixture is stirred for 30 min at 0 degrees and then overnight at room temperature. The reaction solution is concentrated by evaporation and the residue is purified by chromatography on silica gel using methylene chloride/methanol (3–10%) as the eluent.

EXAMPLE 2

In order to determine the inhibitory potential of compounds of the general formula I on MMPs such as HNC, the catalytic domain is incubated (isolation and purification see Schnierer, S., Kleine, T., Gote, T., Hillemann, A., Knäuper, V., Tschesche, H., Biochem. Biophys. Res. Commun. (1993), 191, 319–326). Subsequently the initial reaction rate of a standard substrate is measured as described in Grams F. et al., FEBS 335 (1993) 76–80). The results are evaluated in the usual manner (see e.g. Dixon, M., Biochem. J. (1953) 55, 170–202).

The synthetic collagenase substrate is a heptapeptide coupled C-terminally with dinitrophenol (DNP). This DNP residue quenches the fluorescence of the Trp of the heptapeptide. After cleavage of a tripeptide containing the DNP residue, the measurable fluorescence increases.

Assay buffer:
50 mM Tris/HCl pH 7.6 (Tris=Tris-(hydroxymethyl)-aminomethane)
100 mM NaCl/10 mM $CaCl_2$/5% MeOH (if required)
enzyme:
8 nM catalytic domain (Met80-Gly242) of the human neutrophilic collagenase (MMP8)
Substrate:
10 μM DNP-Pro-Leu-Gly-Leu-Trp-Ala-D-Arg-NH2
total assay volume:
1 ml A solution of enzyme and inhibitor is prepared in assay buffer at 25° C. The reaction is started by addition of the substrate to the solution. The cleavage of the fluorogenic substrate is measured by fluorescence spectroscopy (excitation and emission wavelength at 280 and 350 nm respectively). The IC50 value is determined for an inhibitor concentration at which the reaction rate is halved.

The compounds of the general formula I act as inhibitors.

The assay was also carried out with the enzymes MMP2 and MMP1 in analogy to the example described above with HNC (MMP8) but at other concentrations and in this case the compound of example 1.5 was compared with Marimastat. An activation is additionally necessary for MMP2 and MMP1. This showed a clear selectivity advantage relative to MMP1.

TABLE

|  | MMP8 IC50 [nM] | MMP2 IC50 [nM] | MMP1 inhibition at 200 nM |
|---|---|---|---|
| Marimastat* | 12 | 14 | 100% |
| example 1.5 | 18 | 23 | 20% |

*N2-[3S-hydroxy-4- (N-hydroxyamino)-2R-isobutyl-succinyl)-L-tert-leucine-N1-methylamide Whereas the inhibitors inhibit MMp2 and MMp8 to an almost equal extent, the inhibition of MMp1 by the compound of example 1.5 according to the invention is substantially poorer than by Marimastat.

What is claimed is:
1. A compound of formula (I)

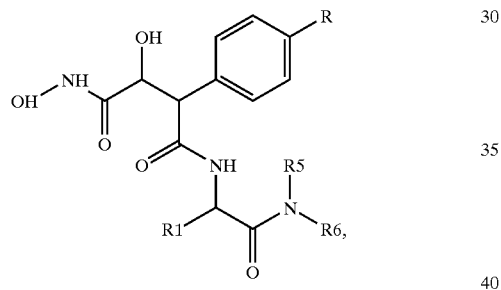

wherein
R is selected from the group consisting of a straight-chained or branched, saturated or unsaturated residue containing 1 to 8 carbon atoms which is uninterrupted or interrupted by 1 or 2 heteroatoms selected from the group consisting of O, N and S, cyclopentyl, cyclohexyl, cycloheptyl, morpholinyl, thiamorpholinyl, piperidinyl, piperazinyl, tetrahydrofiuyl, tetrahydropyranyl, phenyl, naphthyl, pyridinyl, pyrimidinyl, pyridazinyl, pyrazinyl, imidazolyl, furanyl, oxazolyl, isothiazolyl, isooxazolyl, 1,2,3-triazolyl, 1,2,4-triazolyl, thiazolyl, indolyl, tetrahydronaphthyl, decalinyl, quinolyl, isoquinolyl, tetrahydroquinolyl, tetrahydroisoquinolyl, benzimidazolyl, indazolyl, oxindolyl, benzofuranyl, benzothienyl, benzthiazolyl, benzoxazolyl, purinyl, phenoxy, naphthoxy, pyridinyl-oxy, pyrimidinyl-oxy, pyridazinyl-oxy, pyrazinyl-oxy, imidazolyl-oxy, furanyl-oxy, oxazolyl-oxy, isothiazolyl-oxy, isooxazolyl-oxy, 1,2,3-triazolyl-oxy, 1,2,4-triazolyl-oxy, thiazolyl-oxy, indolyl-oxy, tetrahydronaphthoxy, decalinyl-oxy, quinolinyl-oxy, isoquinolinyl-oxy, tetrahydroquinolinyl-oxy, tetrahydroisoquinolinyl-oxy, benzimidazolyl-oxy, indazolyl-oxy, oxindolyl-oxy, benzofuranyl-oxy, benzothienyl-oxy, benzthiazolyl-oxy, benzoxazolyl-oxy, purinyl-oxy, phenyl-$C_1$–$C_2$ alkyl and naphthyl-$C_1$–$C_2$ alkyl, wherein the residues for R listed above are each independently unsubstituted or substituted with 1–3 substituents each independently selected from the group consisting of halogen, hydroxy, mercapto, $C_1$–$C_3$ alkyl, $C_3$–$C_8$ cycloalkyl, $C_4$–$C_8$ cycloalkenyl, hydroxy-$C_1$–$C_3$ alkyl, $C_1$–$C_3$ alkoxy, hydroxy-$C_1$–$C_3$ alkoxy, chloro-$C_1$–$C_3$ alkoxy, $C_1$–$C_3$ alkylmercapto, $C_1$–$C_3$ alkylsulfinyl, $C_1$–$C_3$ alkylsulfonyl, amino, $C_1$–$C_3$ alkylamino, di-$C_1$–$C_3$-alkylamino, nitro, carboxyl, carboxamido, $C_1$–$C_3$ alkoxycarbonyl, $C_1$–$C_3$ alkoxycarbonyl-$C_1$–$C_3$ alkyl, perfluoro-$C_1$–$C_3$ alkyl and aminocarbonyl, wherein the amino and aminocarbonyl substituents are each unsubstituted or substituted with 1–2 substituents each independently selected from the group consisting of $C_1$–$C_6$ alkyl, nitrile, oxo and alkanoyl of 1–3 carbons;
R1 is selected from the group consisting of a straight-chained or branched, saturated or unsaturated residue containing 1 to 8 carbon atoms which is uninterrupted or interrupted by 1 or 2 heteroatoms selected from the group consisting of O, N and S, cyclopentyl, cyclohexyl, cycloheptyl, morpholinyl, thiamorpholinyl, piperidinyl, piperazinyl, tetrahydrofuryl, tetrahydropyranyl, phenyl, naphthyl, pyridinyl, pyrimidinyl, pyridazinyl, pyrazinyl, imidazolyl, furanyl, oxazolyl, isothiazolyl, isooxazolyl, 1,2,3-triazolyl, 1,2,4-triazolyl, thiazolyl, indolyl, tetrahydronaphthyl, decalinyl, quinolyl, isoquinolyl, tetrahydroquinolyl, tetrahydroisoquinolyl, benzimidazolyl, indazolyl, oxindolyl, benzofuranyl, benzothienyl, benzthiazolyl, benzoxazolyl, purinyl, phenyl-$C_1$–$C_2$ alkyl and naphthyl-$C_1$–$C_3$ alkyl, $C_1$–$C_3$ alkyl-pyridinyl, $C_1$–$C_3$ alkyl-pyrimidinyl, $C_1$–$C_3$ alkyl-pyridazinyl, $C_1$–$C_3$ alkyl-pyrazinyl, $C_1$–$C_3$ alkyl-imidazolyl, $C_1$–$C_3$ alkyl-furanyl, $C_1$–$C_3$ alkyl-oxazolyl, $C_1$–$C_3$ alkyl-isothiazolyl, $C_1$–$C_3$ alkyl-isooxazolyl, $C_1$–$C_3$ alkyl-1,2,3-triazolyl, $C_1$–$C_3$ alkyl-1,2,4-triazolyl, $C_1$–$C_3$ alkyl-thiazolyl, $C_1$–$C_3$ alkyl-mercaptophenyl and $C_1$–$C_3$ alkyl-indolyl, wherein the residues for R1 listed above are each independently unsubstituted or substituted with 1–3 substituents each independently selected from the group consisting of halogen, hydroxy, mercapto, alkylmercapto $C_1$–$C_3$ alkyl, $C_3$–$C_8$ cycloalkyl, $C_4$–$C_8$ cycloalkenyl, hydroxy-$C_1$–$C_3$ alkyl, $C_1$–$C_3$ alkoxy, hydroxy-$C_1$–$C_3$ alkoxy, chloro-$C_1$–$C_3$ alkoxy, $C_1$–$C_3$ alkylmercapto, $C_1$–$C_3$ alkylsulfinyl, $C_1$–$C_3$ alkylsulfonyl, amino, $C_1$–$C_3$ alkylamino, $C_1$–$C_3$ dialkylamino, nitro, carboxyl, carboxamido, $C_1$—$C_3$ alkoxycarbonyl, $C_1$–$C_3$ alkoxycarbonyl-$C_1$–$C_3$ alkyl, perfluoro-$C_1$–$C_3$ alkyl and aminocarbonyl, wherein the amino and aminocarbonyl substituents are each unsubstituted or substituted with 1–2 substituents each independently selected from the group consisting of $C_1$–$C_6$ alkyl, nitrile, oxo and alkanoyl of 1—3 carbons;
R5 is hydrogen or a straight-chained or branched, saturated or unsaturated residue containing 1 to 8 carbon atoms which is uninterrupted or interrupted by 1 or 2 heteroatoms selected from the group consisting of O, N and S and
R6 is selected from the group consisting of hydrogen, a straight-chained or branched, saturated or unsaturated residue containing 1 to 8 carbon atoms which is uninterrupted or interrupted by 1 or 2 heteroatoms selected from the group consisting of O, N and S, cyclopentyl, cyclohexyl, cycloheptyl, morpholinyl, thiamorpholinyl, piperidinyl, piperazinyl, tetrahydrofuryl, tetrahydropyranyl, phenyl, naphthyl, pyridinyl, pyrimidinyl, pyridazinyl, pyrazinyl, imidazolyl, furanyl, oxazolyl, isothiazolyl, isooxazolyl, 1,2,3-triazolyl, 1,2,4-triazolyl, thiazolyl, indolyl, tetrahydronaphthyl, decalinyl, quinolyl, isoquinolyl, tetrahydroquinolyl, tetrahydroisoquinolyl, benzimidazolyl, indazolyl, oxindolyl, benzofuranyl, benzothienyl, benzthiazolyl, benzoxazolyl, purinyl, phenyl-$C_1$–$C_2$ alkyl and naphthyl-$C_1$–$C_2$ alkyl, $C_1$–$C_3$ alkyl-pyridinyl, $C_1$–$C_3$ alkyl-pyrimidinyl, $C_1$–$C_3$ alkyl-pyridazinyl, $C_1$–$C_3$ alkyl-pyrazinyl, $C_1$–$C_3$ alkyl-imidazolyl, $C_1$–$C_3$ alkyl-furanyl, $C_1$–$C_3$ alkyl-oxazolyl, $C_1$–$C_3$ alkyl-isothiazolyl, $C_1$–$C_3$ alkyl-isooxazolyl, $C_1$–$C_3$ alkyl-1,2,3-triazolyl, $C_1$–$C_3$ alkyl-1,2,4-triazolyl, $C_1$–$C_3$ alkyl-thiazolyl, $C_1$–$C_3$ alkyl-mercaptophenyl and $C_1$–$C_3$ alkyl-indolyl, wherein the residues for R6 listed above are each independently unsubstituted or substituted with 1–3 substituents each independently selected from the group consisting of halogen, hydroxy, mercapto, alkylmercapto $C_1$–$C_3$ alkyl, $C_3$–$C_8$ cycloalkyl, $C_4$–$C_8$ cycloalkenyl, hydroxy-$C_1$–$C_3$ alkyl, $C_1$–$C_3$ alkoxy, hydroxy-$C_1$–$C_3$ alkoxy, chloro-$C_1$–$C_3$ alkoxy, $C_1$–$C_3$ alkylmercapto, $C_1$–$C_3$ alkylsulfinyl, $C_1$–$C_3$ alkylsulfonyl, amino, $C_1$–$C_3$ alkylamino, $C_1$–$C_3$ dialkylamino, nitro, carboxyl, carboxamido, $C_1$–$C_3$ alkoxycarbonyl, $C_1$–$C_3$ alkoxycarbonyl-$C_1$–$C_3$ alkyl, perfluoro-$C_1$–$C_3$ alkyl and aminocarbonyl, wherein the amino and aminocarbonyl substituents are each unsubstituted or substituted with 1–2 substituents each independently selected from the group consisting of $C_1$–$C_6$ alkyl, nitrile, oxo and alkanoyl of 1–3 carbons, or R5 and R6, together with the N atom to which they are bound, form a saturated or unsaturated 5-membered or 6-membered ring which contains 0 or 1 additional heteroatoms selected from the group consisting of oxygen, nitrogen and sulfur, the remainder of the atoms in the ring being carbon, or a pharmacologically acceptable salt, ester, optical isomer or prodrug thereof.

2. The compound of claim 1, wherein R is selected from the group consisting of —O-phenyl-R2, phenyl-R2, n-butyloxy and hexyloxy, wherein R2 is selected from the group consisting of hydrogen, halogen, methyl and hydroxy.

3. The compound of claim 2, wherein R is selected from the group consisting of —O-phenyl, phenyl and n-butyloxy.

4. The compound of claim 1, wherein R1 is selected from the group consisting of benzyl, phenyl, tert-butyl and C(CH$_3$)$_2$OMe.

5. The compound of claim 4, wherein R1 is tert-butyl.

6. The compound of claim 1, wherein R5 is selected from the group consisting of hydrogen, methyl and ethyl.

7. The compound of claim 6, wherein R5 is hydrogen.

8. The compound of claim 1, wherein R6 is selected from the group consisting of methyl, ethyl, phenyl and pyridyl.

9. The compound of claim 1, wherein R5 and R6, together with the N atom to which they are bound, form a saturated or unsaturated 5-membered or 6-membered ring which contains an additional oxygen atom, the remainder of the atoms in the ring being carbon.

10. The compound of claim 9, wherein R5 and R6, together with the N atom to which they are bound, form a morpholinyl ring.

11. The compound of claim 1, wherein the compound is in the following isomeric form:

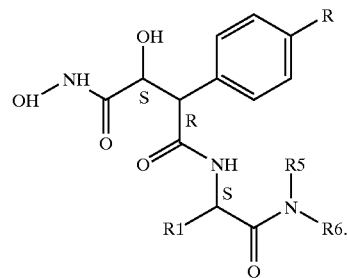

12. The compound of claim 1, wherein R is a residue which provides a clogP value of 2.0 to 6.0, as determined using a compound having the formula

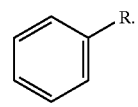

13. The compound of claim 1, wherein R1 is a residue which provides a clogP value of –1.5 to 2.0, as determined using a compound having the formula

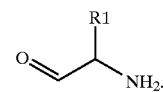

14. A compound of formula (I)

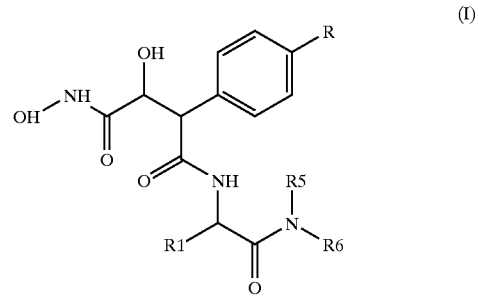

(I)

wherein

R is a residue which provides a clogP value of 2.0 of 6.0, as determined using a compound having the formula

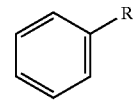

R1 is a residue which provides a clogP value of –1.5 to 2.0, as determined using a compound having the formula

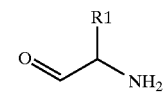

R5 is hydrogen or a straight-chained or branched, saturated or unsaturated residue containing 1 to 8 carbon atoms which is uninterrupted or interrupted by 1 or 2 heteroatoms selected from the group consisting of O, N and S and R6 is selected from the group consisting of hydrogen, a straight-chained or branched, saturated or unsaturated residue containing 1 to 8 carbon atoms which is uninterrupted or interrupted by 1 or 2 heteroatoms selected from the group consisting of O, N and S, cyclopentyl, cyclohexyl, cycloheptyl, morpholinyl, thiamorpholinyl, piperidinyl, piperazinyl, tetrahydro fury 1, tetrahydropyranyl, phenyl, naphthyl, pyridinyl, pyrimidinyl, pyridazinyl, pyrazinyl, imidazolyl, furanyl, oxazolyl, isothiazolyl, isooxazolyl, 1,2,3-triazolyl, 1,2,4-triazolyl, thiazolyl, indolyl, tetrahydronaphthyl, decalinyl, quinolyl, isoquinolyl, tetrahydroquinolyl, tetrahydroisoquinolyl, benzimidazolyl, indazolyl, oxindolyl, benzofuranyl, benzothienyl, benzthiazolyl, benzoxazolyl, purinyl, phenyl-$C_1$–$C_2$ alkyl and naphthyl-$C_1$–$C_2$ alkyl, $C_1$–$C_3$ alkyl-pyridinyl, $C_1$–$C_3$ alkyl-pyrimidinyl, $C_1$–$C_3$ alkyl-pyridazinyl, $C_1$–$C_3$ alkyl-pyrazinyl, $C_1$–$C_3$ alkyl-imidazolyl, $C_1$–$C_3$ alkyl-furanyl, $C_1$–$C_3$ alkyl-oxazolyl, $C_1$–$C_3$ alkyl-isothiazolyl, $C_1$–$C_3$ alkyl-isooxazolyl, $C_1$–$C_3$ alkyl-1,2,3-triazolyl, $C_1$–$C_3$ alkyl-1,2,4-triazolyl, $C_1$–$C_3$ alkyl-thiazolyl, $C_1$–$C_3$ alkyl-mercaptophenyl and $C_1$–$C_3$ alkyl-indolyl, wherein the residues for R6 listed above are each independently unsubstituted or substituted with 1–3 substituents each independently selected from the group consisting of halogen, hydroxy, mercapto, alkylmercapto $C_1$–$C_3$ alkyl, $C_3$–$C_8$ cycloalkyl, $C_4$–$C_8$ cycloalkenyl, hydroxy-$C_1$–$C_3$ alkyl, $C_1$–$C_3$ alkoxy, hydroxy-$C_1$–$C_3$ alkoxy, chloro-$C_1$–$C_3$ alkoxy, $C_1$–$C_3$ alkylmercapto, $C_1$–$C_3$ alkylsulfinyl, $C_1$–$C_3$ alkylsulfonyl, amino, $C_1$–$C_3$ alkylamino, $C_1$–$C_3$ dialkylamino, nitro, carboxyl, carboxamido, $C_1$–$C_3$ alkoxycarbonyl, $C_1$–$C_3$ alkoxycarbonyl-$C_1$–$C_3$ alkyl, perfluoro-$C_1$–$C_3$ alkyl and aminocarbonyl, wherein the amino and aminocarbonyl substituents are each unsubstituted or substituted with 1–2 substituents each independently selected from the group consisting of $C_1$–$C_6$ alkyl, nitrile, oxo and alkanoyl of 1–3 carbons or R5 and R6, together with the N atom to which they are bound, form a saturated or unsaturated 5-membered or 6-membered ring which contains 0 or 1 additional heteroatoms selected from the group consisting of oxygen, nitrogen and sulfur, the remainder of the atoms in the ring being carbon, or a pharmacologically acceptable salt, ester, optical isomer or prodrug thereof.

15. A pharmaceutical composition suitable for use as a gelatinase inhibitor, comprising the compound of claim 1 in combination with a pharmaceutically acceptable carrier.

16. A pharmaceutical composition suitable for use as a gelatinase inhibitor, comprising a compound of claim 14 in combination with a pharmaceutically acceptable carrier.

17. A method of treating a disease associated with gelatinase expression in a patient in need of the treatment same, comprising administering to the patient a gelatinase inhibiting-effective amount of the compound of claim 1, wherein the disease is arthritis, corneal ulcer or arteriosclerosis.

18. A method of treating a disease susceptible to treatment by a gelatinase inhibitor in a patient, comprising administering to the patient a gelatinase inhibiting-effective amount of a compound of claim 14, wherein the disease is arthritis, corneal ulcer or arteriosclerosis.

* * * * *